United States Patent
Ibe et al.

(10) Patent No.: US 10,197,916 B2
(45) Date of Patent: Feb. 5, 2019

(54) CURABLE COMPOSITION, RESIST MATERIAL AND RESIST FILM

(71) Applicant: DIC Corporation, Tokyo (JP)

(72) Inventors: Takeshi Ibe, Chiba (JP); Naoto Yagi, Chiba (JP); Hisashi Tanimoto, Chiba (JP); Makoto Yada, Chiba (JP)

(73) Assignee: DIC Corporation, Tokyo (JP)

( * ) Notice: Subject to any disclaimer, the term of this patent is extended or adjusted under 35 U.S.C. 154(b) by 0 days.

(21) Appl. No.: 15/517,806

(22) PCT Filed: Oct. 6, 2015

(86) PCT No.: PCT/JP2015/078321
§ 371 (c)(1),
(2) Date: Apr. 7, 2017

(87) PCT Pub. No.: WO2016/072202
PCT Pub. Date: May 12, 2016

(65) Prior Publication Data
US 2017/0306062 A1   Oct. 26, 2017

(30) Foreign Application Priority Data

Nov. 7, 2014   (JP) .................................. 2014-227003

(51) Int. Cl.
| | | |
|---|---|---|
| *G03F 7/075* | (2006.01) | |
| *C07F 7/18* | (2006.01) | |
| *C08F 30/08* | (2006.01) | |
| *C08F 290/00* | (2006.01) | |
| *C08F 299/08* | (2006.01) | |
| *H01L 21/027* | (2006.01) | |
| *C08F 290/08* | (2006.01) | |
| *C07F 7/21* | (2006.01) | |
| *C08G 77/38* | (2006.01) | |
| *G03F 7/00* | (2006.01) | |
| *G03F 7/027* | (2006.01) | |
| *C08G 77/20* | (2006.01) | |
| *C08G 77/22* | (2006.01) | |
| *C08G 77/26* | (2006.01) | |

(52) U.S. Cl.
CPC .............. *G03F 7/0755* (2013.01); *C07F 7/18* (2013.01); *C07F 7/21* (2013.01); *C08F 30/08* (2013.01); *C08F 290/00* (2013.01); *C08F 290/08* (2013.01); *C08F 299/08* (2013.01); *C08G 77/38* (2013.01); *G03F 7/0002* (2013.01); *G03F 7/027* (2013.01); *H01L 21/027* (2013.01); *C08G 77/20* (2013.01); *C08G 77/22* (2013.01); *C08G 77/26* (2013.01)

(58) Field of Classification Search
CPC .............................. C08F 30/08; C08F 230/08
USPC ........................................................ 526/279
See application file for complete search history.

(56) References Cited

U.S. PATENT DOCUMENTS

| | | | |
|---|---|---|---|
| 2002/0028406 A1* | 3/2002 | Lee ....................... | G03F 7/0758 430/270.1 |
| 2005/0136269 A1 | 6/2005 | Doehler et al. | |
| 2007/0299231 A1 | 12/2007 | Doehler et al. | |
| 2010/0178620 A1* | 7/2010 | Dei ....................... | C09D 183/04 430/325 |
| 2011/0076353 A1 | 3/2011 | Shirai et al. | |
| 2014/0061970 A1 | 3/2014 | Sekine et al. | |

FOREIGN PATENT DOCUMENTS

| | | |
|---|---|---|
| CN | 102236253 A | 11/2011 |
| JP | 2012/124340 A * | 6/2012 |
| JP | 2013-051410 A | 3/2013 |
| KR | 10-2011-0034710 A | 4/2011 |
| WO | 2009/113357 A1 | 9/2009 |
| WO | 2012/111656 A1 | 8/2012 |

OTHER PUBLICATIONS

"Synthesis and Photo-curing Behaviors of Silicon-containing (Vinyl Ether)-(Allyl Ether) Hybrid Monomers" authored by Yuan et al. and published in Polymer International (2013) 62, 1624-1633.*
"Preparation and Electrochemical Properties of an Inorganic-organic Hybrid Polymer Electrolyte" authored by Qiu et al. and published in Gaofenzi Xuebao (2005) 4, 496-500.*
Abstract for JP 2012/0124340 (no date).*
Full translation of "Preparation and Electrochemical Properties of an Inorganic-organic Hybrid Polymer Electrolyte" authored by Qiu et al. and published in Gaofenzi Xuebao (2005) 4, 496-500 (no date).*

(Continued)

*Primary Examiner* — Marc S Zimmer
(74) *Attorney, Agent, or Firm* — McDermott, Will & Emery LLP

(57) ABSTRACT

A problem of The present invention is to provide a curable composition capable of forming a resist which can be easily washed after curing and which has high dry etching resistance and excellent precision of fine pattern transfer, also provide a resist film and a laminate each containing the curable composition, and further provide a pattern forming method using the resist film. The problem of the present invention can be solved by providing a curable composition containing a multifunctional polymerizable monomer (A) which has two or more groups having a polymerizable group and has at least one group Q having a polymerizable group represented by formula (1) below, the amount of silicon atoms in an nonvolatile content being 10 wt % or more.

13 Claims, No Drawings

(56) References Cited

OTHER PUBLICATIONS

Si-yuan Wang and Ying-quan Zou. "The study of synthesis and photocuring behaviors of organic silicon modified methyl acrylate and acrylate." Proceedings of SPIE, vol. 8322, pp. 83222G1-83222G7 (2012).
Search Report issued in corresponding International Patent Application No. PCT/JP2015/078321, dated Jan. 12, 2016.
Chinese Office Action issued in corresponding Chinese Patent Application No. 201580056812.0, dated Aug. 28, 2018, with Engish Translation.

* cited by examiner

CURABLE COMPOSITION, RESIST MATERIAL AND RESIST FILM

CROSS REFERENCE

This application is the U.S. National Phase under 35 U.S.C. § 371 of International Application No. PCT/JP2015/078321, filed on Oct. 6, 2015, which claims the benefit of Japanese Application No. 2014-227003, filed on Nov. 7, 2014, the entire contents of each are hereby incorporated by reference.

TECHNICAL FIELD

The present invention relates to a curable composition, a resist material, and a resist film.

BACKGROUND ART

A ultraviolet (UV) imprint method attracts attention as a fine processing method for effectively producing, at low cost, electronic devices such as a large-scale integrated circuit, a liquid crystal display, and the like, a patterned media, a microchannel device, a biochip, and the like.

The UV imprint method includes transferring a pattern to a substrate by etching using a pattern formed by molding a resist film as a mold. In this method, the resist film having a pattern formed therein is required to have high etching resistance. Known examples of the UV imprint method include a method of directly transferring a pattern to a substrate, a bilayer resist method using a resist film as a first resist layer and a substrate having a second resist layer and an underlayer substrate, and the like. A known example of the bilayer resist layer is a method using a silicon-containing resin for the first resist layer and including transferring a pattern to the second resist layer by etching with oxygen-based gas plasma and transferring the pattern to the underlayer substrate by further etching the second resist layer to which the pattern has been transferred.

A quartz mold is normally used as the mold used in the UV imprint method. The quartz mold satisfactorily transmits UV light and has high hardness and high surface smoothness, and is thus a material suitable for the UV imprint method. However, quartz is difficult to process and thus the quartz mold is more expensive than other mold materials. In addition, the mold is repeatedly used, and the presence of residues on the mold influences pattern formation, thereby causing the need for complete washing. However, the UV imprint method, particularly a nanoimprint method for an ultrafine pattern, has the problem of clogging a mold pattern with a resist cured product.

Therefore, a method of plasma ashing the quartz mold with oxygen gas is used for removing the residues on the mold. However, when a resist resin is a silicon-containing resist, $SiO_2$ is produced by plasma treatment, and there is thus the problem that the residues cannot be removed by plasma ashing treatment.

Also, Patent Literature 1 discloses a method for removing mold residues by using, as a resist, a resin which is solubilized by acid treatment. However, the resin used has low resistance to dry etching with oxygen-based gas because it does not contain silicon and has a low concentration of curable functional groups, thereby causing the possibility of decreasing the precision of pattern transfer to a substrate.

CITATION LIST

Patent Literature

PTL 1: International Publication No. 2009/113357

SUMMARY OF INVENTION

Technical Problem

A problem of the present invention is to provide a curable composition capable of forming a resist which can be easily washed after curing and which has high dry etching resistance and excellent precision of fine pattern transfer.

Solution to Problem

As a result of earnest investigation, the inventors of the present invention found that a composition containing a monomer having a polymerizable group having a specified silicon-containing group can form a resist having which can be easily washed after curing and which has high dry etching resistance and excellent precision of fine pattern transfer.

That is, the present invention provides a curable composition containing a multifunctional polymerizable monomer (A) which has two or more groups having a polymerizable group and has at least one group Q having a polymerizable group represented by formula (1) below, the amount of silicon atoms in a nonvolatile content being 10 wt % or more.

—O—R—Y    (1)

(In the formula (1), an oxygen atom is bonded to a silicon atom, R represents an unsubstituted or substituted alkyl group having 0 to 25 carbon atoms which may contain a heteroatom, and Y represents a polymerizable unsaturated group.)

Also, the present invention provides a curable composition in which the multifunctional monomer (A) contains 5 or more silicon atoms.

Further, the present invention provides a curable composition further containing a monofunctional polymerizable monomer (B) or a multifunctional polymerizable monomer (C) other than (A), wherein the molar ratio between the monomers is (A):(B)=100:0 to 10:90 or (A):(C)=80:20 to 100:0.

Further, the present invention provides a resist material containing the curable composition, a resist film formed by curing the resist material, a laminate formed by laminating the resist film on a substrate, a method for forming a pattern on a substrate by dry etching the laminate, and the resultant pattern formed object.

Advantageous Effects of Invention

A curable composition of the present invention contains silicon atoms in an amount of 10 wt % or more in a nonvolatile content and thus has high dry etching resistance. Also, a group Q having a polymerizable group is a decomposable group, and thus washing can be easily performed by treatment with an acid, alkali, or the like after curing. Further, having a multifunctional polymerizable monomer enables good curability and fine pattern formation.

DESCRIPTION OF EMBODIMENTS

Multifunctional Polymerizable Monomer (A)

A curable composition of the present invention is characterized by containing a multifunctional polymerizable monomer (A). The multifunctional polymerizable monomer (A) of the present invention is a multifunctional polymerizable monomer which has two or more groups having a polymerizable group and has at least one group Q having a polymerizable group represented by formula (1) below.

—O—R—Y    (1)

(In the formula (1), an oxygen atom is bonded to a silicon atom, R represents an unsubstituted or substituted alkyl group having 0 to 25 carbon atoms which may contain a heteroatom, and Y represents a polymerizable group.)

The multifunctional polymerizable monomer (A) has two or more groups having a polymerizable group. The term "polymerizable group" represents a polymerization-reactable functional group, and is specifically a radical-polymerizable group. Examples of the radical-polymerizable group include a vinyl group, a (meth)acryloyl group, an allyl group, an isopropenyl group, a styryl group, a vinyloxy group, a vinyloxycarbonyl group, a vinylcarbonyl group, a N-vinylamino group, and the like. Particularly preferred is a (meth)acryloyl group. The group having a polymerizable group may be a group having any of the polymerizable groups.

The multifunctional polymerizable monomer (A) of the present invention has two or more groups having a polymerizable group and has at least one polymerizable group Q represented by the formula (1). The group Q having a polymerizable group is directly bonded to a silicon atom, and thus dry etching resistance is enhanced. Also, a Si—O—R bond part is decomposable, and thus the bond is decomposed by treatment with an acid, alkali, or the like. In this case, a crosslinked structure is broken, and thus a cured product is dissolved, thereby permitting washing.

The multifunctional polymerizable monomer (A) has at least one group Q having a polymerizable group but preferably has two or more groups Q in order to improve the washability.

Examples of the group Q having a polymerizable group represented by the formula (1) include the following structures.

[Chem. 1]

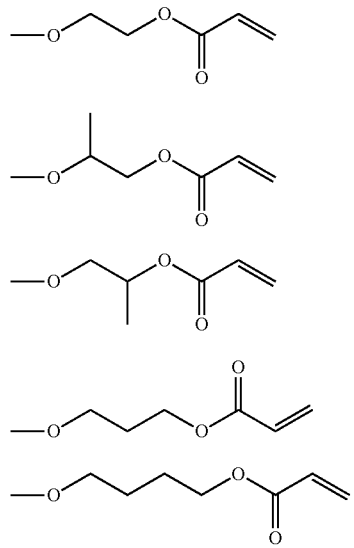

Q-1

Q-2

Q-3

Q-4

Q-5

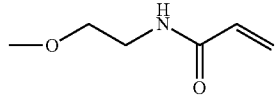

Q-6

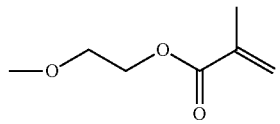

Q-7

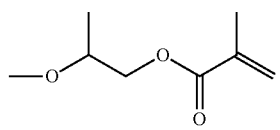

Q-8

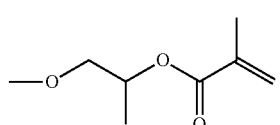

Q-9

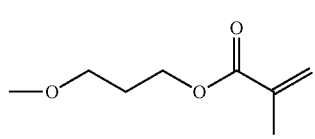

Q-10

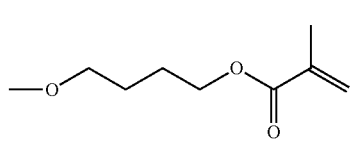

Q-11

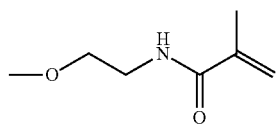

Q-12

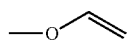

Q-13

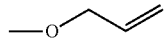

Q-14

Q-15

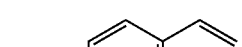

Q-16

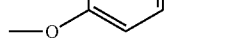

Q-17

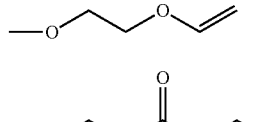

Q-18

Q-19

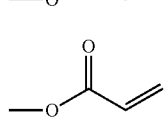

Q-20

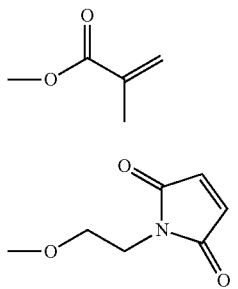
Q-21
Q-22
The multifunctional polymerizable monomer (A) of the present invention may be either linear or branched. Examples thereof include the following structures.
[Chem. 2]
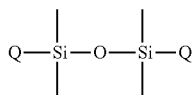
a-1
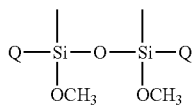
a-2
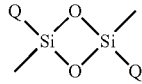
a-3
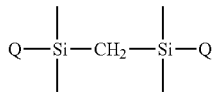
a-4
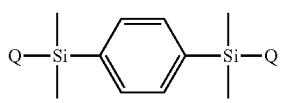
a-5
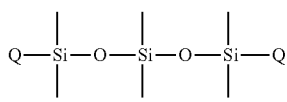
a-6
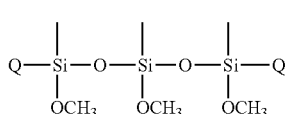
a-7
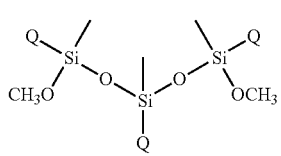
a-8
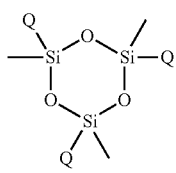
a-9
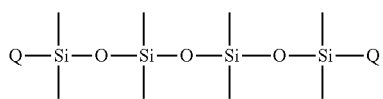
a-10
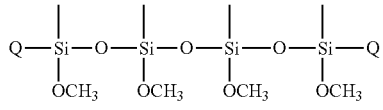
a-11
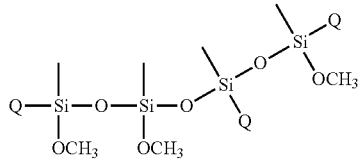
a-12
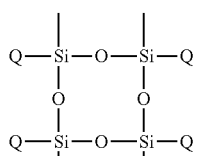
a-13
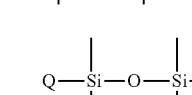
a-14
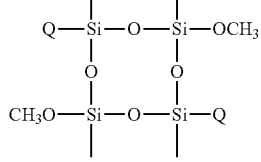
a-15
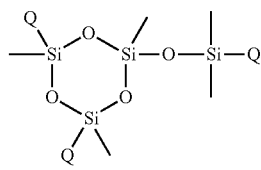
a-16
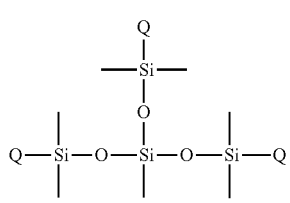
a-17
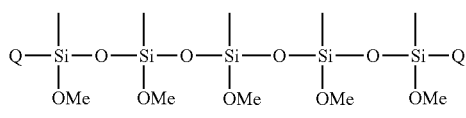
a-18

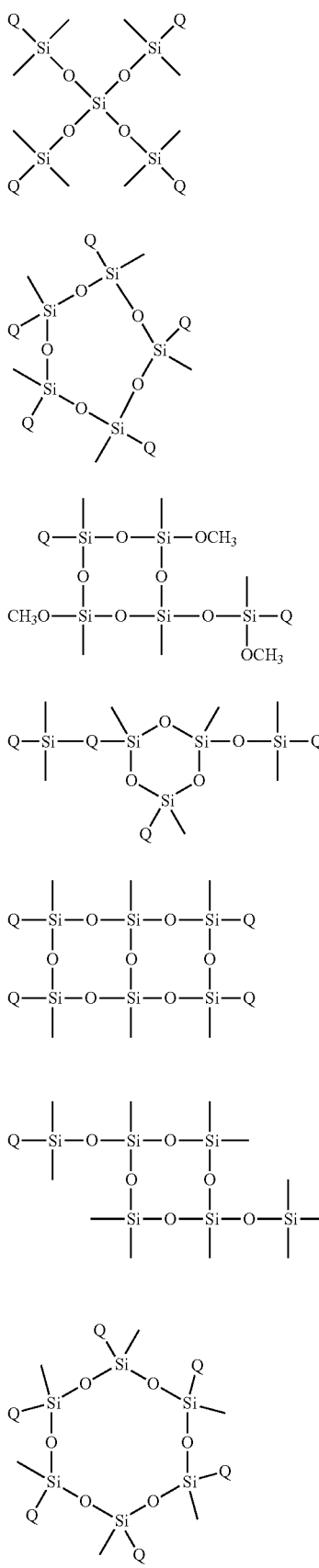
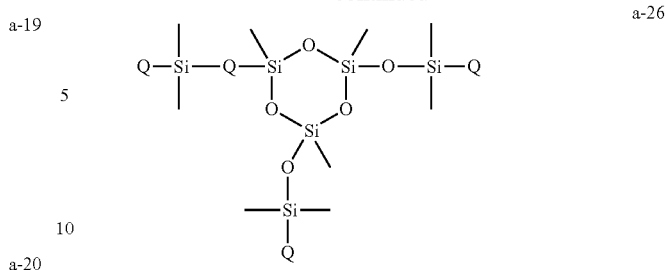

Among these, the multifunctional polymerizable monomer (A) is particularly preferably a structure having 5 or more silicon atoms. This is because having 5 or more silicon atoms improves the dry etching resistance.

Synthesis of the multifunctional polymerizable monomer (A) of the present invention is not particularly limited, and a known common method can be used. Examples of the method include a synthesis method by using a compound having a polymerizable unsaturated group and a hydroxyl group as a raw material and performing dehydrochlorination reaction with chlorosilane, a synthesis method by ester exchange with alkoxysilane, and the like.

Monofunctional Polymerizable Monomer (B)

The curable composition of the present invention may contain a monofunctional polymerizable monomer (B). The monofunctional polymerizable monomer (B) is a compound having one polymerizable group. The term "polymerizable group" represents a polymerization-reactable functional group, and is specifically, for example, a radical-polymerizable group, a cationic-polymerizable group, or the like. The polymerizable group possessed by the monofunctional polymerizable monomer (B) is preferably a group which reacts with the polymerizable group possessed by the multifunctional polymerizable monomer (A), and for example, when the polymerizable group possessed by the multifunctional polymerizable monomer (A) is a (meth)acryloyl group, the polymerizable group possessed by the monofunctional polymerizable monomer (B) is also preferably a (meth)acryloyl group.

Examples of the monofunctional polymerizable monomer (B) include hydroxyethyl (meth)acrylate, hydroxypropyl (meth)acrylate, hydroxybutyl (meth)acrylate, polyethylene glycol mono(meth)acrylate, polypropylene glycol mono (meth)acrylate, benzyl (meth) acrylate, phenylbenzyl (meth) acrylate, phenoxybenzyl (meth)acrylate, phenol EC-modified (meth)acrylate, o-phenylphenol EO-modified (meth) acrylate, para-cumylphenol EO-modified (meth)acrylate, nonylphenol EO-modified (meth)acrylate, phthalic acid monohydroxyethyl (meth) acrylate, 2-hydroxy-3-phenoxypropyl (meth)acrylate, 2-(phenylthio)ethyl (meth)acrylate, cyclohexyl (meth)acrylate, tetrahydrofurfuryl (meth)acrylate, dicyclopentenyl (meth)acrylate, dicyclopentenyloxyethyl (meth)acrylate, dicyclopentanyl meth)acrylate, isobornyl (meth)acrylate, adamantyl (meth)acrylate, and the like. A silicon-containing monomer is particularly preferred. This is because silicon is contained, and thus the dry etching resistance of the curable composition containing the monofunctional polymerizable monomer (B) is improved. Examples of the silicon-containing monomer include vinyltrimethoxysilane, vinyltriethoxysilane, vinylmethyldimethoxysilane, vinyltri(2-methoxyethoxy)silane, vinyltriacetoxysilane, 2-trimethoxysilylethyl vinyl ether, 3-(meth)

acryloyloxypropyl trimethoxysilane, 3-(meth)acryloyloxypropyl triethoxysilane, 3-(meth)acryloyloxypropylmethyl dimethoxysilane, styryl trimethoxysilane, one-terminal reactive silicone oil (X-22-174ASX, X-22-174BX, KF-2012, X-22-2426, X-22-2475, and the like manufactured by Shin-Etsu Chemical Co., Ltd.), and the like.

Multifunctional Polymerizable Monomer (C)

The curable composition of the present invention may contain a multifunctional polymerizable monomer (C) other than the multifunctional polymerizable monomer (A). Examples of the multifunctional polymerizable monomer (C) include 1,2-ethanediol di(meth)acrylate, 1,2-propanediol di(meth)acrylate, 1,4-butanediol di(meth)acrylate, 1,6-hexanediol di(meth)acrylate, dipropylene glycol di(meth)acrylate, neopentylglycol di(meth)acrylate, tripropylene glycol di(meth)acrylate, trimethylolpropane di(meth)acrylate, trimethylolpropane tri(meth)acrylate, tris(2-(meth)acryloyloxy) isocyanurate, pentaerythritol tri(meth)acrylate, pentaerythritol tetra(meth)acrylate, di(trimethylolpropane) tatra(meth)acrylate, di(pentaerythritol) penta(meth)acrylate, di(pentaerythritol) hexa(meth)acrylate, tricyclodecanedimethanol di(meth)acrylate, ethylene oxide-added bisphenol A di(meth)acrylate, ethylene oxide-added bisphenol F di(meth)acrylate, propylene oxide-added bisphenol A di(meth)acrylate, propylene oxide-added bisphenol F di(meth)acrylate, di(meth)acrylate having a 9,9-bisphenylfluorene skeleton, (meth) acrylate-modified silicone (X-22-2445, X-22-1602, X-22-164, X-22-164AS, X-22-164A, X-22-164B, X-22-164C, X-22-164E, KR-513, X-40-2672B, X-40-9272B, and the like manufactured by Shin-Etsu Chemical Co., Ltd.), and (meth)acrylate-modified silsesquioxane (AC-SQ TA-100, MAC-SQ TM-100, AC-SQ SI-20, MAC-SQ SI-20, and the like manufactured by Toagosei Co., Ltd.). Particularly preferred are (meth)acrylate-modified silicone (X-22-2445, X-22-1602, X-22-164, X-22-164AS, X-22-164A, X-22-164B, X-22-164C, X-22-164E, KR-513, X-40-26728, X-40-9272B, and the like manufactured by Shin-Etsu Chemical Co., Ltd.), and (meth)acrylate-modified silsesquioxane (AC-SQ TA-100, MAC-SQ TM-100, AC-SQ SI-20, MAC-SQ SI-20, and the like manufactured by Toagosei Co., Ltd.).

Curable Composition

The curable composition of the present invention is characterized by containing the multifunctional polymerizable monomer (A) and containing silicon atoms in an amount of 10 wt % or more in a nonvolatile content. Since the amount of silicon atoms in the nonvolatile content is 10 wt % or more, the curable composition of the present invention has high dry etching resistance and is thus suitable for a resist for dry etching. The amount of silicon atoms in the nonvolatile content is preferably 15 wt % or more and more preferably 20 wt % or more.

The curable composition of the present invention contains multifunctional polymerizable monomers including the multifunctional polymerizable monomer (A). The amount of the multifunctional polymerizable monomer in a nonvolatile content of the curable composition is preferably 50 wt % or more. This is because excellent pattern formability are exhibited during imprint due to increasing three-dimensional crosslinking points.

When the curable composition of the present invention contains the multifunctional polymerizable monomer (A) and further contains the monofunctional polymerizable monomer (B) or the multifunctional polymerizable monomer (C), the weight ratio between the monomers is preferably (A):(B)=100:0 to 10:90 or (A):(C)=80:20 to 100:0, and more preferably (A):(B)=100:0 to 50:50 or (A):(C)=90:10 to 100:0, and the multifunctional polymerizable monomer (A) is particularly preferably 100%.

The curable composition of the present invention preferably contains a curing catalyst. When the polymerizable monomer has a radical-polymerizable group, the curing catalyst is preferably a radical polymerization initiator. In particular, when imprint is UV imprint, a photoradical polymerization initiator is preferred. These curing catalysts may be used alone or in combination of two or more.

Examples of the photoradical polymerization initiator include 2,2-dimethoxy-1,2-diphenylethan-1-one, 1-hydroxy-cyclohexyl-pneyl-ketone, 1-[4-(2-hydoxyethoxy)-phenyl]-2-hydroxy-2-methyl-1-propan-1-one, 2-methyl-1-[4-(methylthio)phenyl]-2-morpholinopropan-1-one, 2-benzyl-2-dimethylamino-1-(4-morpholinophenyl)-butanone-1, bis(2,4,6-trimethylbenzoyl)-phenylphosphine oxide, 2-hydroxy-1-{4-[4-(2-hydroxy-2-methyl-propionyl)-benzyl]-phenyl}-2-methyl-propane, 1,2-octanedione, 1-[4-(phenylthio)-,2-(O-benzoyloxime)], 2-hydroxy-2-methyl-1-phenyl-propan-1-one, phenylglyoxylic acid methyl ester, 2,4,6-trimethylbenzoyl-diphenyl-phosphine oxide, and the like. The photoradical polymerization initiator is not particularly limited as long as it absorbs light from a light source used for photocuring.

The compounds described above are available as commercial products, and examples thereof include IRGACURE (registered trademark) 651, 184, 2959, 907, 369, 379, 819, 127, and OXE01, DAROCUR (registered trademark) 1173, MBF, and TPO (the above are manufactured by BASF Japan Co., Ltd.), ESACURE (registered trademark) KIP150, TZT, KTO46, 1001M, KB1, KS300, KL200, TPO, ITX, and EDB (the above are manufactured by Nihon Siber Hegner K. K.), and the like.

The content of the curing catalyst in the curable composition of the present invention is preferably 0.5% to 20% by mass and more preferably 1% by mass to 10% by mass relative to the all polymerizable monomers. The content of 0.5% by mass or more increases curability and causes excellent pattern formability.

Also, the curable composition of the present invention may contain a solvent. The viscosity of the curable composition can be adjusted by adding the solvent. Examples of the solvent include aliphatic or alicyclic hydrocarbons such as n-hexane, n-heptane, n-octane, cyclohexane, cyclopentane, and the like; aromatic hydrocarbons such as toluene, xylene, ethylbenzene, anisol, and the like; alcohols such as methanol, ethanol, n-butanol, ethylene glycol monomethyl ether, propylene glycol monomethyl ether, propylene glycol monoethyl ether, and the like; esters such as ethyl acetate, n-butyl acetate, isobutyl acetate, ethylene glycol monomethyl ether acetate, propylene glycol monomethyl ether acetate, and the like; ketones such as acetone, methyl ethyl ketone, methyl isobutyl ketone, cyclohexanone, and the like; alkyl ethers; ethers such as 1,2-dimethoxyethane, tetrahydrofuran, dioxane, and the like; N-methylpyrrolidone; dimethylformamide; and dimethylacetamide. These may be used alone or in combination of two or more.

When the solvent is used, if required, the solvent content can be adjusted so that the content of components other than the solvent in the curable composition is within a range of 0.1% to 100% by mass.

The curable composition of the present invention may contain other compounds within a range in which the effect of the present invention is not impaired. Examples of other compounds include an organic pigment, an inorganic pigment, an extender pigment, an organic filler, an inorganic filler, a photosensitizer, an ultraviolet absorber, an antioxidant, a surfactant, an adhesion auxiliary, and the like.

Any one of a nonionic surfactant, an anionic surfactant, a cationic surfactant, and an amphoteric surfactant may be used as the surfactant, but a nonionic surfactant is preferred in view of compatibility with other components. The content of the surfactant is 0.001% to 10% by mass, preferably 0.01% to 8% by mass, and more preferably 0.1% to 5% by mass relative to the all polymerizable compounds. When two or more types of surfactants are used, the total amount is within the range described above. The surfactant within the range causes excellent coating uniformity and good mold transferability.

Examples of the nonionic surfactant include polyoxyalkylene alkyl ether-based surfactants, polyoxyalkylene fatty acid ester-based surfactants, sorbitan fatty acid ester-based surfactants, polyoxyalkylene alkyl amine-based surfactants, Pluronic (triblock copolymer of polyethylene oxide and polypropylene oxide) surfactants, fluorine-based surfactants, silicone-based surfactants, acrylic polymer-based surfactants, and the like.

Examples of the anionic surfactant include alkylbenzene sulfonate salt-based surfactants, alkyl alcohol sulfate salt-based surfactants, polyoxyalkylene alkyl ether sulfate salt-based surfactants, alkyl alcohol phosphate salt-based surfactants, polyoxyalkylene alkyl ether phosphate salt-based surfactants, polyoxyalkylene alkyl ether acetate salt-based surfactants, fluorine-based surfactants, and the like. An acid type or neutral type may be used.

Examples of the cationic surfactant include tetraalkylammonium halide-based surfactants, alkylpyridinium halide-based surfactants, alkylimidazoline halide-based surfactants, and the like.

Examples of the amphoteric surfactant include alkylbetaine-based surfactants, alkylimidazolium betaine-based surfactants, lecithin-based surfactants, and the like.

Resist Material

A resist material of the present invention contains the curable composition. A resist film can be formed by curing the resist material of the present invention. A resist film in which a pattern has been formed can be formed through a step of forming a pattern in the resist material of the present invention and a step of irradiating the patterned-formed layer with light.

The resist material of the present invention is applied onto a substrate, and then a pattern is formed. A method for applying on a substrate is not particularly limited, and there may be used various methods such as a spray method, a spin coating method, a dip method, a roll coating method, a blade coating method, a doctor roll method, a doctor blade method, a curtain coating method, a slit coating method, a screen printing method, an ink jet method, and the like.

In forming a pattern using a mold, a resist film in which a pattern has been formed is formed by pressing the mold, on which a pattern has been previously formed, on the film formed by the method described above and then curing the film in a state of being in contact with the mold. The resist material of the present invention can also be preferably used particularly for forming a pattern of 100 nm or less.

Examples of a material of the mold for imprint include light-transmitting materials such as quartz, ultraviolet transmitting glass, sapphire, diamond, silicone materials such as polydimethylsiloxane and the like, fluorocarbon resins, cycloolefin resins, other light-transmitting resin materials, and the like. When the substrate used is a light-transmitting material, the mold for imprint may be a material not transmitting light. Examples of the material not transmitting light include metals, SiC, mica, and the like. Among these, a quartz mold is particularly preferred because it satisfactorily transmits ultraviolet light and has high hardness and high surface smoothness.

The mold for imprint can be selected from molds having shapes such as a flat plate shape, a belt shape, a roll shape, a roll belt shape, and the like.

The mold for imprint used may be subjected to mold release treatment for improving mold releasability of the curable composition from the surface of the mold. Examples of the mold release treatment include treatment with a silicone-based or fluorine-based silane coupling agent and the like.

When the mold is a light-transmitting material, a method of light irradiation from the mold side can be used as a method for curing the curable composition, while when the substrate is a light-transmitting material, a method of light irradiation from the substrate side can be used. The light used for light irradiation may be light with which the photopolymerization initiator reacts, and light with a wavelength of 450 nm or less (active energy rays such as ultraviolet rays, X-rays, γ-rays, or the like) is preferred in view of satisfactory reaction with the photopolymerization initiator and the ability of curing at lower temperature.

Also, when there is a problem with followability to a pattern to be formed, heating may be performed to a temperature at which satisfactory flowability can be obtained during light irradiation. The heating temperature is preferably 0° C. to 300° C., more preferably 0° C. to 200° C., still more preferably 0° C. to 150° C., and particularly preferably 25° C. to 80° C. Within the temperature range, the pattern shape formed from the curable composition is precisely maintained.

After curing, the mold is released to produce a resist film in which a convex-concave pattern has been formed by transferring a concave-convex pattern of the mold. In order to suppress deformation such as warping or the like of the substrate and to enhance the precision of the concave-convex pattern, a releasing step is preferably performed by a method of releasing the mold after the temperature of a cured film decreases near room temperature (25° C.)

When a resist residue is confirmed on the mold after release of the mold, washing is performed. Since the mold is repeatedly used, the resist residue on the mold adversely affects pattern formation in a next step.

The multifunctional polymerizable monomer (A) contained in the resist material of the present invention has the polymerizable group-containing group Q. The polymerizable group-containing group Q is a hydrolysable group, and thus the mold is satisfactorily washed by hydrolysis treatment after curing.

Examples of a washing solution capable of hydrolysis used for washing the mold include acid, alkali, hot water, and the like. Examples of an acid washing solution include sulfuric acid, hydrochloric acid, nitric acid, carbonic acid, acetic acid, phosphoric acid, aqua regia, dilute hydrofluoric acid, a sulfuric acid/hydrogen peroxide mixture, a hydrochloric acid/hydrogen peroxide mixture, and the like. Examples of an alkali washing solution include caustic alkalis such as caustic soda, caustic potash, and the like, various inorganic alkalis such as silicic acid salts, phosphoric acid salts, carbonic acid salts, and the like, organic alkalis such as tetramethyl ammonium hydroxide and the like, ammonia water, ammonia hydrogen water, ammonia hydrogen peroxide water, and the like. Since the alkali washing solution may dissolve $SiO_2$, the acid washing solution is preferred for a glass or quartz mold, and the sulfuric acid/hydrogen peroxide mixture is particularly preferred. In particular, when a quartz mold having a fine pattern of 100 nm or less is washed, the mold can be washed by using the acid washing solution without damage to the fine pattern because the alkali washing solution has the possibility of impairing rectangularity of the mold due to the $SiO_2$ dissolving function.

Examples of a washing method include, but are not particularly limited to, spray, shower, immersion, hot-water immersion, ultrasonic immersion, a spin method, bubbling, shaking, brushing, steam, polishing, and the like. In order to prevent re-adhesion of the dirt washed out, the spin method is particularly preferred.

The resist film of the present invention is laminated on a substrate to form a laminate. The substrate which forms the laminate can be selected according to various applications, and examples thereof include quartz, sapphire, glass, plastic, ceramic materials, a vapor-deposited film (CVD, PVD, or sputtering), a magnetic film, a reflective film, metal substrates of Ni, Cu, Cr, Fe, stainless steel, and the like, paper, SOG (Spin On Glass), SOC (Spin On Carbon), polymer substrates such as a polyester film, a polycarbonate film, a polyimide film, and the like, a TFT array substrate, an electrode plate of PDP, conductive substrates of ITO, a metal, and the like, semiconductor-manufacturing substrates such as an insulating substrate, silicon, silicon nitride, polysilicon, silicon oxide, amorphous silicon, and the like.

Also, a substrate for a bilayer resist having a second resist layer and an underlayer substrate may be used. A combination in the substrate for a bilayer resist is not particularly limited, but examples of a material of the second resist layer include metal masks of Cr, Al, Ni, and the like, phenol resins such as novolac resin and the like, vinyl resins such as a hydroxyvinylnaphthalene copolymer, a polyvinylphenol copolymer, and the like, polycyclic aromatic resins such as a nortricyclene copolymer, an indene copolymer, an acenaphthylene copolymer, fullerene derivatives, and the like, SOC layers formed by using cured products of these resins, an amorphous carbon film formed by CVD, and the like. Also, a multilayer substrate in which three or four layers of different materials are laminated may be used, and the resist film of the present invention can be used as an underlayer film.

The shape of the substrate is not particularly limited and may be any one of a plate shape, a sheet shape, a three-dimensional shape which entirely or partially has curvature, and the like according to purposes. Also, the hardness, thickness, etc. of the substrate are not limited.

The laminate of the present invention may be formed by applying the resist material on the substrate and immediately curing the resist material to form the resist film, or the laminate may be formed by separating the resist film formed on a temporary substrate and then attaching the resist film to the substrate. When the resist film has a pattern formed therein, the pattern is transferred to the substrate by dry etching the laminate, thereby producing a pattern-formed object.

The resist film made of the resist material of the present invention has excellent dry etching resistance, and thus deformation or the like of the pattern does not occur during dry etching, and a fine etching pattern of a nano-size can be transferred to the substrate.

A known gas may be used as the gas used for dry etching, and examples of the gas which can be used include oxygen atom-containing gas such as oxygen, carbon monoxide, carbon dioxide, and the like, inert gas such as helium, nitrogen, argon, and the like, chlorine-based gas such as chlorine, boron trichloride, and the like, fluorine gas, fluorocarbon-based gas, hydrogen gas, ammonia gas, and the like. These gases may be used alone or used as a proper mixture.

Etching using the etching gas can form a desired pattern on the substrate.

EXAMPLES

Next, the present invention is specifically described below by examples and comparative examples. In the examples, "parts" and "%" are on a mass basis unless otherwise specified.

The present invention is described in further detail below, but the present invention is not limited to these examples.

Synthesis Example 1

Synthesis of 1,3-bis(acryloyloxyethyloxy)-1,1,3,3-tetramethyl disiloxane (Multifunctional Polymerizable Monomer (A-1)

In a nitrogen atmosphere, 1,3-dichloro-1,1,3,3-tetramethyl disiloxane (4.064 g, 0.02 mol) and triethylamine (4.048 g, 0.04 mol) were dissolved in tetrahydrofuran (60 mL) and the resultant solution was cooled to 0° C. by an ice bath. Then, a tetrahydrofuran (40 mL) solution of 2-hydroxyethyl acrylate (4.644 g, 0.04 mol) was added dropwise to the solution and reacted by stirring at 0° C. for 2 hours. Then, hydrochloride was removed by filtration, and the residue was concentrated by evaporation. The residue was purified by silica gel column chromatography using an ethyl acetate-hexane solvent and subjected to reduced-pressure fractionation to produce 5.42 g (yield 75%) of a multifunctional polymerizable monomer (A-1).

The physical property values of the resultant compound are as follows.

$^1$H-NMR (300 MHz, $CDCl_3$) δ (ppm): 6.42 (dd, 2H, CH=C), 6.16 (m, 2H, C=CH—C=O), 5.87 (dd, 2H, H=C), 4.25 (m, 4H, $CH_2$—O—C=O), 3.90 (m, 4H, $CH_2$—O—Si), 0.12 (m, 12H, Si—$CH_3$).

Synthesis Example 2

Synthesis of 1,5-bis(acryloyloxyethyloxy)-1,1,3,3,5,5-hexamethyl trisiloxane (Multifunctional Polymerizable Monomer (A-2)

Synthesis was performed by the same method as for synthesis of 1,3-bis(acryloyloxyethyloxy)-1,1,3,3-tetramethyl disiloxane. 1,5-Dichloro-1,1,3,3,5,5-hexamethyl trisiloxane was used as a raw material in place of 1,3-dichloro-1,1,3,3-tetramethyl disiloxane.

The physical property values of the resultant compound are as follows.

$^1$H-NMR (300 MHz, $CDCl_3$) δ (ppm): 6.42 (dd, 2H, CH=C), 6.14 (m, 2H, C=CH—C=O), 5.83 (dd, 2H, H=C), 4.25 (m, 4H, CH$_2$—O—C=O), 3.89 (m, 4H, CH$_2$—O—Si), 0.12 (m, 18H, Si—CH$_3$).

Synthesis Example 3

Synthesis of 1,7-bis(acryloyloxyethyloxy)-1,1,3,3,5,5,7,7-octamethyl tetrasiloxane (Multifunctional Polymerizable Monomer (A-3)

Synthesis was performed by the same method as for synthesis of 1,3-bis(acryloyloxyethyloxy)-1,1,3,3-tetramethyl disiloxane. 1,7-Dichloro-1,1,3,3,5,5,7,7-octamethyl tetrasiloxane was used as a raw material in place of 1,3-dichloro-1,1,3,3-tetramethyl disiloxane.

The physical property values of the resultant compound are as follows.

$^1$H-NMR (300 MHz, CDCl$_3$) δ (ppm): 6.42 (dd, 2H, CH=C), 6.14 (m, 2H, C=CH—C=O), 5.83 (dd, 2H, H=C), 4.25 (m, 4H, CH$_2$—O—C=O), 3.89 (m, 4H, CH$_2$—O—Si), 0.12 (m, 24H, Si—CH$_3$).

Synthesis Example 4

Synthesis of Multifunctional Polymerizable Monomer (A-4)

Methyl-based silicone resin KC-89S (trade name, manufactured by Shin-Etsu Chemical Co., Ltd.) (137.9 g), 2-hydroxyethyl acrylate (81.3 g, 0.7 mol), and para-toluene sulfonic acid monohydrate (44 mg) were mixed and the produced methanol was distilled off under reaction at 120° C. Reaction was performed under stirring for 3 hours to produce 197.8 g of multifunctional polymerizable monomer (A-4).

The physical property values of the resultant compound are as follows.

$^1$H-NMR (300 MHz, CDCl$_3$) δ (ppm): 6.43 (m, CH=C), 6.12 (m, C=CH—C=O), 5.83 (m, CH=C), 4.25 (br, CH$_2$—O—C=O), 3.97 (br, CH$_2$—O—Si), 3.52 (s, Si—OCH$_3$), 0.16 (s, Si—CH$_3$). The measurement of weight-average molecular weight showed 770.

Method for Confirming Formation of Polymerizable Group-Containing Group G Represented by Formula (1)

The formation of polymerizable group-containing group G represented by the formula (1) was confirmed by a method described below.

In a $^1$H-NMR spectrum, a peak (δ=3.87 ppm, C—O—C—CH$_2$—) derived from 2-hydroxyethyl acrylate as a raw material disappears, and a peak (δ=3.52, Si—OCH$_3$) of a methoxy group of the methyl-based silicone resin decreases, and thus it was confirmed that alcohol exchange reaction quantitatively proceeds. Also, a new peak (δ=3.97, CH$_2$—O—Si) appears, and thus it was confirmed that 2-hydroxyethyl acrylate and the methyl-based silicone resin are bonded to each other through a Si—O—C bond to form the polymerizable group-containing group Q represented by the formula (1).

Method for Calculating Amount of Silicon Atom

The amount of silicon atoms contained in the multifunctional polymerizable monomer (A-4) was calculated by the following expression.

$$\text{Amount of silicon atom contained in } (A) = E_{Si} \times C_{Silicone} \times M_{Si} \quad \text{[Chem. 3]}$$

$$E_{Si} = (R_{T0}/M_{T0}) + (R_{T1}/M_{T1}) + (R_{T2}/M_{T2}) + (R_{T3}/M_{T3})$$

$$C_{Silicone} = \frac{\text{(Weight of methyl-based silicone resin charged)} - \text{(Weight of methanol distilled off)}}{\text{(Weight of methyl-based silicone resin charged)} + \text{(Weight of 2-hydroxyethylacrylate charged)}}$$

In the expression, $E_{Si}$ is the concentration (eq/g) of silicon atom per g of the silicone resin raw material, $C_{silicone}$ is the amount (wt %) of a portion derived from the silicone resin raw material in the multifunctional polymerizable monomer (A), and $M_{Si}$ is the atomic weight (=28.09) of silicon. $R_{T0}$, $R_{T1}$, $R_{T2}$, and $R_{T3}$ are the molar % ratio of component T0, the molar % ratio of component T1, the molar % ratio of component T2, and the molar % ratio of component T3, respectively, and satisfy ($R_{T0}+R_{T1}+R_{T2}+R_{T3}=1$). $M_{T0}$, $M_{T1}$, $M_{T2}$, and $M_{T3}$ are the unit molecular weight of component T0, the unit molecular weight of component T1, the unit molecular weight of component T2, and the unit molecular weight of component T3, respectively.

Herein, the component T0, the component T1, the component T2, and the component T3 represent the following.

The methyl-based silicone resin used as the raw material is composed of unit T. The unit T represents a unit containing one silicon atom, a methyl group bonded to the silicon atom, and an oxygen atom bonded to another silicon atom or three functional groups not boded to another silicon atom. T0 represents a number of oxygen atoms of 0 bonded to another silicon atom, T1 represents a number of oxygen atoms of 1, T2 represents a number of oxygen atoms of 2, and T3 represents a number of oxygen atoms of 3. The molar % ratio of T0/T1/T2/T3 can be calculated from an integration ratio of a $^{29}$Si-NMR spectrum (single pulse method).

Method for Calculating Number of Silicon Atoms Contained in One Molecule of Multifunctional Polymerizable Monomer (A)

The number of silicon atoms contained in one molecule of oligomer is not changed before and after alcohol exchange reaction. Therefore, the number of silicon atoms contained in one molecule of the silicone resin used as the raw material was calculated by an expression below, and the same value was calculated as the number of silicon atoms contained in one molecule of the multifunctional polymerizable monomer (A-4).

$$\text{Number of silicon atoms contained in one molecule of } (A) = M_W \times E_{Si} \quad \text{[Chem. 4]}$$

In the expression, the value of weight-average molecular weight of silicone resin as the raw material was used as $M_W$.

Number of Polymerizable Group-Containing Groups Q Represented by Formula (1)

The number of polymerizable group-containing groups Q represented by formula (1) contained in one molecule of the multifunctional polymerizable monomer (A-4) was calculated by the following expression.

$$\text{Number of polymerizable group-containing groups Q represented by formula (1)} = (N_{Alkoxy}) \times (1 - R_{trans})$$

$$N_{Alkoxy} = (M_W \times C_{Alkoxy})/M_{Alkoxy} \quad \text{[Chem. 5]}$$

In the expression, $N_{Alkoxy}$ is the number of alkoxy groups in one molecule of the silicone resin raw material, $R_{trans}$ is the conversion rate of alcohol exchange reaction, $M_{Alkoxy}$ is the molecular weight (g/mol) of an alkoxy group in the silicone resin raw material, and $C_{Alkoxy}$ is the amount (wt %) of alkoxy groups in the silicone resin raw material. $R_{trans}$ can be calculated from a $^1$H-NMR spectrum of the multifunctional polymerizable monomer (A-4) using an integration ratio of a peak (δ=3.52, Si—OCH$_3$) of a methoxy group and an integration ratio of a peak (δ=3.97, CH$_2$—O—Si) of bonding between 2-hydroxyethyl acrylate and the methyl-based silicone resin through a Si—O—C bond.

Synthesis Example 5

Synthesis of Multifunctional Polymerizable Monomer (A-5)

Methyl-based silicone resin KR-500 (trade name, manufactured by Shin-Etsu Chemical Co., Ltd.) (110.8 g), 2-hydroxyethyl acrylate (58.1 g, 0.5 mol), and para-toluene sulfonic acid monohydrate (34 mg) were mixed and the produced methanol was distilled off under reaction at 120° C. Reaction was performed under stirring for 3 hours to produce 153.9 g of multifunctional polymerizable monomer (A-5).

The physical property values of the resultant compound are as follows.

$^1$H-NMR (300 MHz, CDCl$_3$) δ (ppm): 6.43 (m, CH═C), 6.13 (m, C═CH—C═O), 5.83 (m, CH═C), 4.25 (br, CH$_2$—O—C═O), 3.96 (br, CH$_2$—O—Si), 3.50 (s, Si—OCH$_3$), 0.15 (s, Si—CH$_3$). Measurement of the weight-average molecular weight showed 1650.

Formation of the polymerizable group-containing group Q represented by the formula (1), the amount of silicon atoms contained in the multifunctional polymerizable monomer (A-5), the number of silicon atoms contained in one molecule of the multifunctional polymerizable monomer (A-5), and the number of the polymerizable group-containing groups Q represented by the formula (1) contained in one molecule of the multifunctional polymerizable monomer (A-5) were calculated by the same methods as in Synthesis Example 4.

Synthesis Example 6

Synthesis of Multifunctional Polymerizable monomer (A-6)

Methyl-based silicone resin X-40-9225 (trade name, manufactured by Shin-Etsu Chemical Co., Ltd.) (129.3 g), 2-hydroxyethyl acrylate (58.1 g, 0.5 mol), and para-toluene sulfonic acid monohydrate (38 mg) were mixed and the produced methanol was distilled off under reaction at 120° C. Reaction was performed under stirring for 3 hours to produce 172.4 g of multifunctional polymerizable monomer (A-6).

The physical property values of the resultant compound are as follows.

$^1$H-NMR (300 MHz, CDCl$_3$) δ (ppm): 6.43 (m, CH═C), 6.13 (m, C═CH—C═O), 5.83 (m, CH═C), 4.24 (br, CH$_2$—O—C═O), 3.95 (br, CH$_2$—O—Si), 3.48 (s, Si—OCH$_3$), 0.15 (s, Si—CH$_3$). Measurement of the weight-average molecular weight showed 3580.

Formation of the polymerizable group-containing group Q represented by the formula (1), the amount of silicon atom contained in the multifunctional polymerizable monomer (A-6), the number of silicon atoms contained in one molecule of the multifunctional polymerizable monomer (A-6), and the number of the polymerizable group-containing groups Q represented by the formula (1) contained in one molecule of the multifunctional polymerizable monomer (A-6) were calculated by the same methods as in Synthesis Example 4.

Multifunctional Polymerizable Monomer (A)

Specific structures of the multifunctional polymerizable monomer (A) include structural formulae below.

[Chem. 6]

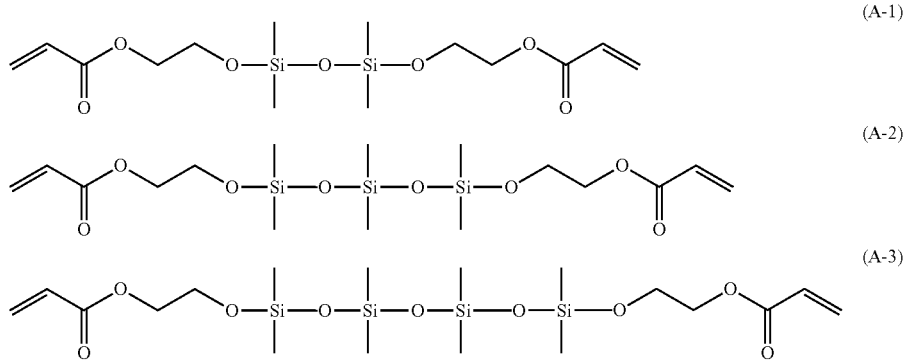

(A-1)

(A-2)

(A-3)

2-Hydroxyethyl acrylate-modified silicone resin . . . (A-4)
2-Hydroxyethyl acrylate-modified silicone resin . . . (A-5)
2-Hydroxyethyl acrylate-modified silicone resin . . . (A-6)

Comparative Monomer (R)

[Chem. 7]

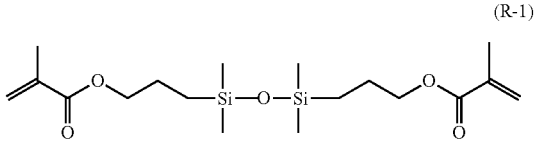

(R-1)

R-1: Both-terminal methacryl-modified silicone (X-22-164: manufactured by Shi-Etsu Chemical Co., Ltd., containing two silicon atoms in one molecule)

The number of polymerizable groups represented by the formula (1) and the amount and number of silicon atoms contained in the multifunctional polymerizable monomer (A) are summarized in Table 1.

TABLE 1

|     | Number of polymerizable group-containing groups Q represented by formula (1) | Amount of silicon atoms (wt %) | Number of silicon atoms in one molecule |
|-----|---|---|---|
| A-1 | 2    | 15.5 | 2    |
| A-2 | 2    | 19.3 | 3    |
| A-3 | 2    | 22.0 | 4    |
| A-4 | 3.2  | 21.4 | 6.0  |
| A-5 | 5.1  | 25.4 | 17.5 |
| A-6 | 11.3 | 28.7 | 47.4 |
| R-1 | 0    | 14.5 | 2    |

Monofunctional Polymerizable Monomer (B)

B-1: Acryloyloxypropyl trimethoxysilane (KBM-5103: manufactured by Shi-Etsu Chemical Co., Ltd.)

B-2: Benzyl acrylate (Biscoat #160: manufactured by Osaka Organic Chemical Industry Ltd.)

Multifunctional Polymerizable Monomer (C)

C-1: Trimethylolpropane triacrylate (Biscoat #295: manufactured by Osaka Organic Chemical Industry Ltd.)

C-2: Compound described in Synthesis Example 7

Synthesis Example 7

Synthesis of Multifunctional Polymerizable Monomer (C-2)

1,3-Adamantanedicarboxylic acid (1.9 g, 8.5 mmol) was placed in a flask, and thionyl chloride (25 mL) was added under nitrogen. The contents in the flask were refluxed for 3 hours, and then excessive thionyl chloride was distilled off. The residue was evaporated to dryness to produce a white solid of tricyclo[3.3.1.13,7]decane-1,3-dicarbonyl dichloride. Then, 2-vinyloxyethanol (2.0 g, 22.7 mmol), triethylamine (4.0 mL), and chloroform (10 mL) were placed in a three-neck flask, and a chloroform (15 mL) solution of tricyclo[3.3.1.13,7]decane-1,3-dicarbonyl dichloride (2.1 g, 8.1 mmol) was added dropwisely to the flask at 0° C. under nitrogen and then stirred at room temperature for 18 hours. The reaction mixture was placed in a separation funnel and washed with 1M hydrochloric acid until it become neutral and then washed with a saturated aqueous sodium bicarbonate solution and ion exchange water. An organic layer was separated and dried with anhydrous magnesium sulfate, and the solvent was distilled off. The residual colorless transparent liquid was purified by a silica gel medium-pressure column (developing solvent: chloroform) to produce a colorless viscous liquid of tricyclo[3.3.1.13,7]-decane-1,3-dicarboxylic acid bis(2-vinyloxyethylene) ester. Under nitrogen, a THF (6 mL) solution of p-toluenesulfonic acid (36 mg, 0.21 mmol) and methacrylic acid (1.08 g, 12.6 mmol) were placed in a three-neck flask, and 10 mL of a HTF solution of tricycle[3,3,1,13.7]decane-1,3-dicarboxylic acid bis(2-vinyloxyethylene) ester (1.53 g, 4.2 mmol) was placed in the three-neck flask, followed by stirring in a water bath for 6 hours. Then, THF was distilled off from the reaction mixture by using an evaporator, and then diethyl ether was added. The resultant diethyl ether solution was placed in a separation funnel and washed three times with each of a saturated aqueous sodium bicarbonate solution and saturated saline. An organic layer was separated and dried with anhydrous magnesium sulfate, and the solvent was distilled off by an evaporator. The residual colorless transparent liquid was purified by a silica gel medium-pressure column (developing solvent: chloroform) to produce a colorless viscous liquid of multifunctional polymerizable monomer (C-2).

The physical property values of the resultant compound are as follows.

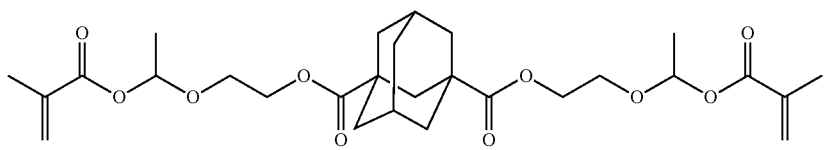

(C-2)

$^1$H-NMR (300 MHz, CDCl$_3$) δ (ppm): 6.1, 5.6 (4H, s, CH$_2$=C), 6.0-5.9 (2H, m, O—CH(CH$_3$)—O), 4.2 (4H, t, —C(=O)—CH$_2$—), 3.8-3.6 (4H, m, —CH$_2$—O) 1.6-2.1 (14H, m, adamantane), 1.9 (6H, s, —CH$_3$), 1.3 (6H, m, O—CH(CH$_3$)—O).

Examples 1 to 8 and Comparative Examples 1 to 4

Preparation of Curable Composition

In Examples 1 to 8 and Comparative Examples 1 to 4, components were mixed based on mixing amounts (parts by weight) shown in Table 2 described below, 2 parts by weight of 2-benzyl-2-dimethylamino-1-(4-morpholinophenyl)-1-butanone (Irgacure-369: manufactured by BASF Corporation) was added as a photopolymerization initiator, and 4-methoxyphenol was further added as a polymerization inhibitor so that the amount was 200 ppm relative to the polymerizable monomers. The each of the resultant mixtures was filtered with a tetrafluoroethylene filter of 0.1 µm to prepare a curable composition.

TABLE 2

| | Multifunctional polymerizable monomer (A) | Comparative monomer (R) | Monofunctional polymerizable monomer (B) | Multifunctional polymerizable monomer (C) | Amount of silicon atom in composition (wt %) | Number of silicon atoms in one molecule of (A) | Number of polymerizable group-containing groups Q represented by formula (1) |
|---|---|---|---|---|---|---|---|
| Example 1 | A-1 (100) | | | | 15.2 | 2 | 2 |
| Example 2 | A-2 (100) | | | | 18.9 | 3 | 2 |
| Example 3 | A-3 (100) | | | | 21.6 | 4 | 2 |
| Example 4 | A-4 (100) | | | | 20.9 | 6.0 | 3.2 |
| Example 5 | A-5 (100) | | | | 24.9 | 17.5 | 5.1 |
| Example 6 | A-6 (100) | | | | 28.1 | 47.4 | 11.3 |
| Example 7 | A-5 (80) | | B-1 (10) | C-1 (10) | 21.1 | 17.5 | 5.1 |
| Example 8 | A-5 (30) | | B-1 (65) | C-1 (5) | 15.1 | 17.5 | 5.1 |
| Comparative Example 1 | | R-1 (100) | | | 14.2 | 2 | 0 |
| Comparative Example 2 | A-1 (30) | | B-2 (65) | C-1 (5) | 4.6 | 2 | 2 |
| Comparative Example 3 | | | B-1 (100) | | 11.8 | — | — |
| Comparative Example 4 | | | | C-2 (100) | 0 | — | — |

Evaluation of Sulfuric Acid/Hydrogen Peroxide Mixture Immersion

Formation of Resist Film

Each of the compositions prepared in Examples 1 to 8 and Comparative Examples 1 to 4 was diluted with a methyl isobutyl ketone solvent and then applied by spin coating on a quartz substrate so that the thickness was 1.0 μm. The resultant laminate was cured in a nitrogen atmosphere by light irradiation with a light quantity of 1000 mJ/cm² from the resin composition side by using a LED light source (manufactured by Ushio Inc.) having a peak wavelength of 365±5 nm, thereby forming a cured film.

Evaluation of Sulfuric Acid/Hydrogen Peroxide Mixture Immersion

The resultant cured film was immersed in a sulfuric acid/hydrogen peroxide mixture (sulfuric acid:hydrogen peroxide water=4:1 (ratio by volume)) for 5 minutes and then rinsed with ion exchange water for 30 seconds, and the residual cured film was visually observed to evaluate the washability of the cured film as follows.
A: The cured film was dissolved in the sulfuric acid/hydrogen peroxide mixture without remaining on the quartz substrate.
B: The cured film was separated from the quartz substrate without remaining on the quartz substrate.
C: The cured film was not changed.

Evaluation of Quartz Mold Washability

Formation of Clogged Quartz Mold

Each of the compositions described in Examples 1 to 8 and Comparative Examples 1 to 4 was applied to a mold (manufactured by NTT Advanced Technology Corporation, NIM-PHL45) made of a quartz material and having a pattern with a line space of 45 to 100 nm and a groove depth of 100 nm to clog the pattern of the mold. The resultant mold was cured by light irradiation in a nitrogen atmosphere with a light quantity of 1000 mJ/cm² from the pattern surface side of the mold by using a LED light source (manufactured by Ushio Inc.) having a peak wavelength of 365±5 nm, thereby producing a clogged quartz mold.

Evaluation of Quartz Mold Washability

The resultant clogged quartz mold was immersed in a sulfuric acid/hydrogen peroxide mixture (sulfuric acid:hydrogen peroxide water=4:1 (ratio by volume)) for 5 minutes, rinsed with ion exchange water for 30 seconds, and then dries with nitrogen gas. A section of the line pattern shape of the mold was observed with a scanning electron microscope to evaluate the washability of the quartz mold as follows.

In observation of a section of the pattern of the mold by using a scanning electron microscope, the evaluation was as follows.
A: The pattern was not clogged over the entire surface.
B: The pattern was partially clogged with a cured product.

Evaluation of Imprint Pattern Formability

One μL of each of the curable compositions prepared in Examples 1 to 8 and Comparative Examples 1 to 4 was dropped on a silicon wafer substrate and set on a lower stage of a nano-imprint apparatus X300 manufactured by SCIVAX Corp. A mold (manufactured by NTT Advanced Technology Corporation, NIM-PHL45) made of a quartz material and having a pattern with a line space of 45 to 100 nm and a groove depth of 100 nm was set on an upper stage of the apparatus. The inside of the apparatus was evacuated, and then the mold was pressure-bonded to the substrate under a pressure of 1.5 atm at room temperature. Then, the mold was exposed to light from the mold back surface by using a LED light source having a peak wavelength of 365±5 nm under a condition of 1000 mJ/cm², and the mold was separated to form a pattern on the substrate. A section of the line pattern was observed with a scanning electron microscope to evaluate the pattern formability as follows.

In observation of the pattern section with a scanning electron microscope, the evaluation was as follows.
A: Pattern loss or falling is less than 1%.
B: Pattern loss or falling is 1% or more and less than 5%.
C: Pattern loss or falling is 5% or more.

Formation of Resist Film

Each of the compositions prepared in Examples 1 to 8 and Comparative Examples 1 to 4 was diluted with a methyl isobutyl ketone solvent and then applied on a silicon wafer substrate by spin coating so that the thickness was 0.2 μm. The resultant laminate was cured in a nitrogen atmosphere by light irradiation with a light quantity of 1000 mJ/cm² from the resin composition side by using a LED light source (manufactured by Ushio Inc.) having a peak wavelength of 365±5 nm, thereby forming a cured film.

Evaluation-1 of O₂-Based Plasma Etching Resistance

The resultant cured film was etched with oxygen plasma for 180 seconds under vacuum of 0.1 Pa by using a dry etcher RIE-101ipH manufactured by SAMCO Inc. and supplying a mixed gas of $O_2/N_2=10/10$ (sccm). The thickness of the remaining cured film was measured and an etching rate per second was calculated. The calculated etching rate was standardized so that the value of etching rate of Example 1 was 1. It is thus shown that the smaller the standardized value, the more excellent the dry etching resistance.

The results are shown in Table 3 below.

TABLE 3

| | Evaluation of sulfuric acid/hydrogen peroxide mixture immersion | Evaluation of quartz mold washability | Evaluation of pattern formability | Evaluation of O₂-based plasma etching resistance |
|---|---|---|---|---|
| Example 1 | A | A | A | 1 (standard value) |
| Example 2 | A | A | A | 0.91 |
| Example 3 | A | A | A | 0.83 |
| Example 4 | A | A | A | 0.56 |
| Example 5 | A | A | A | 0.47 |
| Example 6 | A | A | A | 0.39 |
| Example 7 | B | A | A | 0.65 |
| Example 8 | B | A | B | 0.85 |
| Comparative Example 1 | C | B | A | 1.02 |
| Comparative Example 2 | B | A | B | 3.47 |
| Comparative Example 3 | A | A | C | 1.15 |
| Comparative Example 4 | A | A | A | 8.69 |

INDUSTRIAL APPLICABILITY

A curable composition of the present invention can be used for various imprint technologies, and particularly preferably can be used as a curable composition for forming a nano-size fine pattern. Specifically, the curable composition can be used for producing a semiconductor integrated circuit, a micro electro mechanical system (MEMS), a sensor element, an optical disk, magnetic recording media such as a high-density memory disk, and the like, optical components such as a diffraction grating, a relief hologram, and the like, a nano-device, an optical device, an optical film and polarizing element for producing a flat panel display, a thin-film transistor of a liquid crystal display, an organic transistor, a color filter, an overcoat layer, a microlens array, an immunological analysis chip, a DNA separation chip, a micro reactor, a nano-biodevice, a light guide, an optical filter, a photonic liquid crystal, a shaped object formed by 3D printing, and the like.

The invention claimed is:

1. A curable composition comprising a multifunctional, silicon-containing, polymerizable monomer (A) having two or more groups having a polymerizable group and at least one group Q having a polymerizable group represented by formula (1) below, wherein the amount of silicon atoms in an nonvolatile content is 10 wt % or more,

$$—O—R_n—Y \qquad (1)$$

wherein, in formula (1), the oxygen atom is bonded to a silicon atom, R represents an unsubstituted or substituted alkyl group having 1 to 25 carbon atoms which may contain a heteroatom, n is 0 or 1, and Y represents a polymerizable group, and wherein the multifunctional polymerizable monomer (A) includes an Si—O—CH₃ group.

2. The curable composition according to claim 1, wherein the multifunctional polymerizable monomer (A) contains 5 or more silicon atoms.

3. The curable composition according to claim 1, wherein the multifunctional polymerizable monomer (A) has two or more groups having a polymerizable group represented by the formula (1).

4. The curable composition according to claim 1, wherein the amount of the multifunctional polymerizable monomer is 50% by weight or more relative to the total amount of the polymerizable monomers.

5. A resist material comprising the curable composition according to claim 1.

6. A resist film formed by curing the resist material according to claim 5.

7. The resist film according to claim 6, wherein a pattern is formed.

8. The resist film according to claim 7, wherein the pattern is a non-imprint pattern.

9. A laminate formed by laminating the resist film according to claim 6 on a substrate.

10. A pattern forming method comprising forming a pattern on a substrate by dry etching the substrate using as a mask the pattern formed in the resist film laminated in the laminate according to claim 9.

11. A molded product formed by curing the curable composition according to claim 1.

12. The curable composition according to claim 1, wherein the multifunctional polymerizable monomer (A) has greater than three groups Q.

13. A curable composition comprising a multifunctional, silicon-containing, polymerizable monomer (A) having two or more groups having a polymerizable group and at least one group Q having a polymerizable group represented by formula (1) below, wherein the amount of silicon atoms in an nonvolatile content is 10 wt % or more,

$$—O—R_n—Y \qquad (1)$$

wherein, in formula (1), the oxygen atom is bonded to a silicon atom, R represents an unsubstituted or substituted alkyl group having 1 to 25 carbon atoms which may contain a heteroatom, n is 0 or 1, and Y represents a polymerizable group, and wherein the multifunctional polymerizable monomer (A) includes an Si-alkoxy group.

* * * * *